United States Patent [19]

Pierpoint

[11] 4,427,574

[45] Jan. 24, 1984

[54] CATALYSTS

[75] Inventor: Edward K. Pierpoint, Largs, Scotland

[73] Assignee: Imperial Chemical Industries PLC, London, England

[21] Appl. No.: 388,168

[22] Filed: Jun. 14, 1982

[30] Foreign Application Priority Data

Aug. 14, 1981 [GB] United Kingdom ............. 8124940
Aug. 21, 1981 [GB] United Kingdom ............. 8125678

[51] Int. Cl.$^3$ .............................................. B01J 31/30
[52] U.S. Cl. ..................................... 502/154; 528/15; 502/158
[58] Field of Search ................................... 252/429 R

[56] References Cited

U.S. PATENT DOCUMENTS 3,775,452 11/1973 Karstedt ................ 252/429 R X

FOREIGN PATENT DOCUMENTS 1060420 3/1967 United Kingdom .
1127675 9/1968 United Kingdom .
1211699 11/1970 United Kingdom .

Primary Examiner—Patrick Garvin
Attorney, Agent, or Firm—Cushman, Darby & Cushman

[57] ABSTRACT

A platinum catalyst which comprises the admixture of of
(a) a haloplatinum compound
(b) an aliphatically unsaturated organosiloxane compound and
(c) an aluminium alkoxide.

These catalysts give high activity in promoting reactions of Si-H compounds with unsaturated groups of Si-OH. They are valuable in producing cured organopolysiloxanes such as release coatings.

They are characterized by storage stability and freedom from corrosion of metallic containers.

6 Claims, No Drawings

CATALYSTS

This invention relates to catalysts in particular platinum catalysts for use in promoting the reaction between compounds containing Si-H groups and aliphatically unsaturated groups or silanol groups.

The reaction between Si-H groups and aliphatically unsaturated groups or silanol groups is well known and widely used e.g. in the formation of cured organopolysiloxane. Such cured organopolysiloxanes may be obtained by the reaction of an organopolysiloxane having a plurality of Si-H groups with an organopolysiloxane having a plurality of aliphatically unsaturated groups or SiOH groups. These materials are often elastomeric in character and are used in various applications such as encapsulating compositions and coatings e.g. antistick or release coatings on various substrates. To obtain rapid cure i.e. the reaction between the precursor organopolysiloxane leading to cured product, it is usual to employ a catalyst and platinum or one of its compounds are well known for this function.

In addition to platinum metal and simple inorganic compounds of platinum e.g. chloroplatinic acid and its salts, various complexes of platinum have been proposed as catalysts. UK Pat. No. 1060420 describes complexes of platinum with organosiloxanes bearing vinyl groups prepared by reacting the organosiloxane compound e.g. tetramethyltetravinyl cyclotetrasiloxane with a platinum halide or a platinous complex of a simple unsaturated compound e.g. the complex of cyclohexene or ethylene and platinous chloride. UK Pat. No. 1127675 similarly describes catalysts from the interaction of vinyl organosiloxanes and chloroplatinic acid, any acidity being removable by water washing. UK Pat. No. 1211699 describes platinum siloxane complexes from which essentially all the halogen is removed this being said to improve the catalytic powers.

The known catalysts may exhibit one or more disadvantages. Their activity may be low or vary on storage, in some instances they may be acidic resulting in corrosion of storage containers or the halogen removal or washing in their manufacture can be a troublesome procedure. We have discovered platinum catalysts which can often avoid some or all of these disadvantages.

According to the present invention there is provided a platinum catalyst which comprises the admixture of
(a) a haloplatinum compound
(b) an aliphatically unsaturated organosiloxane compound and
(c) an aluminium alkoxide.

The term "admixture" is used to indicate that the three components (a), (b) and (c) are brought together and does not mean they necessarily remain as a simple mixture. On the contrary it is believed that reactions take place generating new chemical species. Without restricting our invention to any theory it is believed that the components (a) and (b) react to form a complex usually with the concomitant formation of silicon halide groups which in turn react with the aluminium alkoxide. There are no steps taken to remove any component from the admixture but it will be appreciated that any especially volatile material generated may be lost, at least to some degree.

The platinum catalysts of the present invention may be prepared by simply mixing the components (a), (b) and (c). The order of mixing is not critical and it is often convenient to carry out the preparation in a solvent, which may be, but usually is not removed. Suitable solvents include hydrocarbons e.g. toluene, xylene, hexane, heptane. It is sometimes convenient to use an excess of the organosiloxane (b) to serve as solvent.

Catalytic activity changes usually increasing in the period following mixing and this is believed to be due, amongst other things, to components (a) and (b) reacting together. Whilst heating to speed up the attainment of ultimate level of activity is desirable it is not essential.

Typical methods of preparing the platinum catalysts of the present invention include mixing all three components at essentially the same time usually in solvent and either heating for a short period or storing at room temperature. Alternatively components (a) and (b) may be heated together for a period before adding component (c) usually as the mixture is cooling.

When heating is employed temperatures will typically be in the range 50°-150° C., often the reflux temperature of any solvent present. Heating between 10 to 60 minutes is usually adequate to achieve a stable level of catalytic activity.

As examples of haloplatinum compounds which can be used to provide component (a) there may be mentioned chloroplatinic acid and alkali metal salts thereof, platinic chloride $PtCl_4$, platinous chloride $PtCl_2$ and derived acids and salts e.g. $H_2PtCl_4$ and $Na_2PtCl_4$ and platinum complexes such as those from platinous chloride and olefins such as ethylene, propylene, cyclohexene and styrene, e.g. $[(CH_2=CH_2) PtCl_2]_2$, $[(C_6H_{10}) PtCl_2]_2$, and from platinous chloride and dialkylsulphides e.g. $[(C_2H_5)_2S]_2 PtCl_2$. Analogous bromo compounds may be used in place of the aforementioned chloro compounds.

Many more specific examples will be apparent from the extensive literature on platinum compounds and their use as catalysts for many reactions.

The aliphatically unsaturated organopolysiloxane used to provide component (b) will be characterised by having one or more structural units which may be represented by

(1)

or

(2)

in which R is an hydrocarbon radical having aliphatic unsaturation e.g. a vinyl or allyl group, $R_1$ and $R_2$ are either the same as R or are the same or different hydrocarbon radicals without aliphatic unsaturation e.g. $CH_3$, $C_2H_5$ or phenyl. It is usually preferred that R, $R_1$ and $R_2$ are unsubstituted but they may have substituents such as chloro or cyano. Although not usually preferred it is possible that some or all of the groups represented above by $R_1$ and $R_2$ may be halogen atoms e.g. Cl or OH or hydrocarbonoxy groups e.g. $OCH_3$, $OC_2H_5$, $OC_6H_5$.

The materials to provide component (b) may be composed entirely of units of formulae (1) and/or (2) given above, for example divinyltetramethyldisiloxane and linear vinyl dimethylsilyl ended polymethylvinyl siloxanes or cyclic methylvinyl polysiloxanes such as methylvinylcyclotetrasiloxane. Alternatively they may be copolymers having one or more units of formulae (1) and/or (2) with other units of the general formula:

 (3)

or

 (4)

where $R_3$, $R_4$ and $R_5$ have the meanings given above for $R_1$ and $R_2$ when different to R. In such copolymers it is preferred that at least one -SiR.O.SiR- unit is present.

The relative numbers of units of formulae (1) and (2) to those of formulae (3) and (4) in the copolymer can vary widely as can the molecular weight of the copolymer. It is usually preferred that from 20 to 95% of the units are of formula (1) or (2) and the molecular weight ranges from 260 to 100,000. Especially preferred siloxanes are divinyltetramethyldisiloxane and 1:3:5:7-tetramethyl-1:3:5:7-tetravinylcyclotetrasiloxane.

The aluminium alkoxide to provide component (c) will usually be a compound with three alkoxy groups per aluminium atom though it is possible these may be partially replaced by other atoms or groups such as Cl or OH. The alkoxy groups may be the same or different. Examples of suitable aluminium alkoxides include aluminium trimethoxide, aluminium triethoxide, aluminium triisopropoxide, aluminium tri-tert.butoxide, aluminium mono sec.butoxide diisopropoxide aluminium tri-sec.butoxide. Particularly preferred are aluminium triisopropoxide alone or in mixtures with aluminium tri-sec.butoxide or the multi component mixtures of the various species resulting from forming alkoxides of aluminium with a mixture of isopropanol and secondary butanol.

It is usually desirable to select the alkoxy groups such that the aluminium alkoxide has a good degree of solubility in component (b) or in a mixture of (b) with any solvent which may be added.

The relative amounts of components (a), (b) and (c) in the platinum catalysts of the present invention can vary widely. In general there will be sufficient of organosiloxane (b) to provide at least one preferably at least two or more aliphatically unsaturated groups per platinum atom in the haloplatinum compound (a). The amount of aluminium alkoxide (c) will usually be such as to contain at least one aluminium atom per chlorine atom in (a) and preferably several times this amount i.e. ratios of aluminium to chlorine atoms can be from 1:1 to 20:1 or greater. However no significant benefits are obtained by going beyond 20:1. The preferred ratio is from 2:1 to 5:1.

Typical weight proportions in the platinum catalysts of the present invention will be 1 part of component (a), 30 to 300 parts of component (b) and 1 to 10 parts of component (c).

When the platinum catalyst of the present invention is prepared in a solvent there will usually be from 0.025 to 0.5% of platinum expressed as metal in the total weight of the catalyst plus solvent though obviously other proportions can be prepared and used if desired.

The platinum catalysts of the present invention are useful for promoting the reaction between SiH containing compounds and compounds containing aliphatic unsaturation. The extensive scope of such reactions is discussed in UK Pat. Nos. 804097 and 1041082. The catalysts are particularly useful for promoting the formation of cured organopolysiloxanes. The processes of reacting SiH containing compounds and unsaturated compounds and especially of forming cured organopolysiloxanes under the influence of platinum catalysts of the present invention are further features of the present invention. Yet further features are the curable compositions used in the process of forming cured organopolysiloxanes.

Cured organopolysiloxanes are well known and are produced from curable compositions typically containing (i) an organopolysiloxane containing Si-H groups,
(ii) an organopolysiloxane containing Si-Vinyl or Si-allyl groups or Si-OH groups,
(iii) a catalyst for the reaction between (i) and (ii).

The organopolysiloxanes defined by (i) and (ii) above are usually liquid but may be hydrocarbon soluble resinous or solid materials and are well known and readily available from commercial sources. The organo groups attached to silicon can be selected from a wide variety of alkyl, alkenyl, aryl or substituted alkyl groups but for ease of availability organo groups in the organopolysiloxane, other than allyl, vinyl or OH, will normally be solely a lower alkyl, especially methyl or mainly be lower alkyl together with a minor proportion of phenyl groups. The preferred liquid organopolysiloxanes containing Si-H groups are represented by the formulae:

and

where a and c are 0 or an integer and b is an integer of at least 2, having a viscosity at 20° C. of from 10 to 500 cP.

The preferred resinous or solid organopolysiloxanes containing SiH groups consist of copolymers containing the units (a) $(CH_3)_3SiO_{\frac{1}{2}}$, (b) $HSi(CH_3)_2O$ and (c) $SiO_2$, in which the ratio of (b) to (c) is from 0.4:1 to 1.2:1 and the ratio of (a) to (c) is from 1.5:1 to 2.2:1 and th ratio of (a)+(b) to (c) is from 2.4:1 to 3.0:1.

The vinyl or allyl groups in the organopolysiloxanes containing these groups can be attached to any of the silicon atoms forming the polysiloxane. The vinyl or allyl group preferably represent from 0.01 to 5% of the total silicon-bonded radicals, and even more preferably at least 80% of the remaining silicon-bonded radicals are methyl groups.

The preferred organopolysiloxanes of this kind contain vinyl groups and are for example copolymers of dimethylsiloxane units and methylvinyl siloxane units, end stopping by trimethylsilyl, dimethylvinyl silyl or less preferred phenyldimethylsilyl units. Such polysiloxanes may be liquid and will usually have viscosities of from $10^2$ to $10^8$ cP at 20° C. or they may be resinous or solid vinylsiloxanes composed of units (a) $(CH_3)_3SiO_{\frac{1}{2}}$, (b) $CH_2=CH(CH_3)_2SiO_{\frac{1}{2}}$ and (c) $SiO_2$, where the ratio of (a) and (b) units to (c) units is from 0.6:1 to 1.1:1.

The organopolysiloxanes containing Si-OH groups are preferably linear or substantially linear α,ω-dihydroxypolydimethylsiloxanes which may contain a minor proportion of the methyl groups replaced by other alkyl or by phenyl groups, and which have a minimum viscosity at 20° C. of 40 cP.

The relative amounts of the organopolysiloxanes defined above under (i) and (ii), will usually vary between 80 to 99 parts of the organopolysiloxane containing Si-Vinyl or Si-allyl groups or Si-OH groups with 20 to 1 parts of the organopolysiloxane containing Si-H groups. There may be a substantial molar excess of either reactive group and proportions are selected to give desired properties in the cured composition rather than a close stoichiometric balance.

The curable compositions of the present invention are compositions defined above in which the catalyst (iii) is a platinum catalyst of the present invention.

Preferred curable compositions are those in which the component (ii) is an organopolysiloxane containing Si-Vinyl groups.

The curable organopolysiloxane composition of the present invention may be used to yield, as a further feature of the invention, cured materials in a variety of forms. The cured materials are usually of an elastomeric character and may be in the form of castings e.g. for encapsulating electrical components, sealants or coatings on textiles to provide water proofing. However the curable compositions of the present invention are especially valuable in producing release coating. Curing is normally achieved by heating the curable composition e.g. at 50°-200° C. especially 70°-130° C.

Thus the invention also provides a process for coating a substrate with an organopolysiloxane release coating which comprises applying to the substrate the curable organopolysiloxane composition of the present invention and heating to a temperature sufficient to cure the composition to a solid film.

The curable organopolysiloxane may be applied as such but it is often found desirable to apply it in the form of a solution in volatile solvents which are volatilised from the coated film before and/or during the heating to cure the film.

Suitable solvents include toluene, xylene, hexane, white spirits and mixtures of these. The amount of solvent used will be sufficient to lower the viscosity of the organopolysiloxane composition to a level appropriate to the coating technique to be used for its application.

The solvent may be allowed to evaporate at room temperature or this may be facilitated by gentle heating e.g. at 50° C.-100° C.

In carrying out the process for coating a substrate of the invention, the curable organopolysiloxane coating composition may be applied by any suitable method to the substrate, e.g. by spraying, dipping, knife coating, roll coating, reverse roll coating or by gravure cylinders, and may be cured by any suitable means, for example, by heating by hot air, infra-red or UV radiation, the conditions chosen in any specific case being dependent on the nature of the composition used. The temperature selected for curing in any specific case will be governed by the application for which the composition is being used.

The composition of the invention can be cured to non-migratory films having excellent release properties by applying to a substrate and thereafter exposing to a temperature of, for example, 150° C. or higher for a few seconds or to a lower temperature for a longer period, for example, some 10 seconds at 120° C. or about 1 minute at 70° C. The substrate to which the composition is applied may be any solid surface on which it is desired to confer release properties. Suitable substrates include glass, stone and ceramics, plastics including polyolefin and polyester films and fabrics, for example polyethylene, polypropylene and polyethylene terephthalate films and fabrics, cellulosic materials including films and fabrics such as wool, cotton and paper including glassine, parchment, kraft and tissue, and metals such as aluminium foil. The compositions are, however, particularly valuable for use in processes such as paper treating which can be carried out continuously at speeds where it is possible to give a dwell time of some 5-30 seconds in a heating zone at 110°-120° C.

Foils especially papers, coated with a release coating by the process of the present invention form a further feature of the invention and are valuable in providing protective strippable cover e.g. for self adhesive labels or floor tiles, or as a temporary support for isolated films of adhesive before transfering to substrates to be joined.

The platinum catalysts of the present invention are usually characterised by being simple to prepare and may be stored without corrosion of metallic containers and/or loss of catalytic power. They usually show a high level of activity in promoting the cure of organopolysiloxanes and are especially valuable in the preparation of release coated substrates.

The invention is illustrated by the following Examples in which parts are by weight.

EXAMPLE 1

A solution of 3.0 parts cyclohexeneplatinous chloride dimer, 456.0 parts divinyltetramethyldisiloxane and 2541.0 parts toluene are heated to reflux for 15 minutes. After standing overnight at room temperature a 305.0 parts portion is removed and placed in a bottle to which was added 1.4 parts of a mixture of aluminium triisopropoxide and aluminium tri-sec.butoxide, 50:50 wt/wt. This mixture of aluminium alkoxide is available under the trade name "Aliso B" from Manchem Limited, Manchester, England. The bottle is sealed and shaken to give a solution completely free of suspended solid. This solution is Sample A. A second sample, Sample B, is similarly transferred to a bottle, sealed and shaken. No additions are made to Sample B. The chloride contents of the two samples are determined by potentiometric titration of a mixture in n-hexanol and acetone with a solution of silver nitrate in isopropanol. The method is an adaptation of that of Hana and Jura, Anal. Chem. (1959), 1820. Sample A has a chloride content of 185 p.p.m.; Sample B 172 p.p.m. The theoretical chloride value, for 2Cl:Pt, is 204 p.p.m. After storage for 30 days at ambient temperature, 18°-21° C., the catalytic activities of the samples are compared by determining their influence on the gelation times of a cross linkable vinylsiloxane/SiH siloxane composition. The mixture catalysed with Sample A has a gelation time of 33.7 minutes, whilst the mixture containing Sample B has a gelation time of 41.5 minutes. The samples A and B are added in such amounts as to give 10 p.p.m. of platinum on the siloxane content of the cross linkable composition. The gelation times are measured with a Techne Gelation Timer No. 4, available from Techne (Cambridge) Ltd., Cambridge, England. The cross linkable composition used is a 30% wt:wt solution in toluene of a mixture of a vinyl ended dimethylpolysiloxane gum containing 0.8 mole % vinyl groups attached to silicon and a methylhydrogenpolysiloxane fluid. The solution has a viscosity of $14 \times 10^3$ cP at 20° C. Such a mixture of polymers is representative of many commercially available siloxane compositions which cross link to form elastomers in the presence of platinum catalysts. The gelation times are determined with the Gelation Timer No.4 using 75 parts of the polymer solution in an aluminium beaker 4.5 cm×8.0 cm at 20±1° C.

EXAMPLE 2

A mixture of 0.553 parts cyclohexeneplatinous chloride dimer, 41.5 parts 1:3:5:7-tetramethyl-1:3:5:7-tetravinylcyclotetrasiloxane and 511.0 parts toluene are refluxed for 15 minutes. After cooling the solution is divided into two unequal portions, A and B, each of which is placed in a glass container. To portion A (437 parts) is added 19.7 parts of a 10% wt/wt solution of "Aliso B" in toluene and the container then sealed. After 2 days portions of both A and B are withdrawn and their activity compared by determining gelation times as described in Example 1. Sample A gave a gel time of 30.7 minutes whereas Sample B gave a gel time of 57.3 minutes. After a further 21 days the samples are again compared. Sample A gave a gel time of 28.8 minutes, Sample B 143 minutes. Their behaviour as catalysts for a coating composition is also compared as described below.

A solution of a coating composition is prepared from 30 parts of a linear polysiloxane composed of 99.2 mole % dimethylsiloxanyl units and 0.8 mole % methylvinylsiloxanyl units, end stoppered with vinyldimethylsilyl groups, the copolymer having a viscosity of about $15 \times 10^6$ cP, 0.64 parts of a polymethylhydrogensiloxane end stoppered with trimethylsilyl groups and having a viscosity of 22 cP, 76 parts of toluene and 300 parts of n-hexane. This solution is divided into two equal portions each of 203 parts. To the first portion is added 2.10 parts of catalyst Sample A. The resulting catalysed mixture is "Solution C". To the second portion of 203 parts of polymer solution are added 2.10 parts of catalyst Sample B, to give a catalysed coating composition, "Solution D". Each of the coating compositions contains about 75 p.p.m. platinum based on the weight of siloxane polymers, and each is approximately a 7.5% wt:wt solution of silicone polymers in solvent. Each solution is applied to one side of an unprimed highly beaten highly calendered kraft paper, frequently referred to as a glassine paper, such that the resultant coated paper carries about 0.7 to 1.0 gm of siloxane polymer per square meter. Coated papers are heated in an oven at 80° C. for various times. The minimum residence time in the oven to produce a coating which showed no smear upon rubbing with a finger is taken to be the "minimum cure time" for this composition. Coating Solution C has a minimum cure time of 13 seconds. Coating Solution D gives bad smearing after 15 seconds and still shows some smearing after residence times of 60 seconds. Papers coated with Composition C possessed good release properties against pressure sensitive adhesives.

EXAMPLE 3

0.147 Parts cyclohexeneplatinous chloride dimer are dissolved in a mixture of 124.8 parts of toluene and 22.05 parts divinyltetramethyldisiloxane. This solution is not heated but divided into two portions. To 77.7 parts of this solution are then added 3.5 parts of a 10% wt:wt solution of "Aliso B" in toluene. This solution and the untreated remainder are stood at room temperature, 18°-20° C., and samples removed from each for the gelation time test 10 minutes, 6 days and 14 days after the preparation. The following gelation times are observed.

|  | Gelation time, minutes Age of sample at room temp. | | |
| --- | --- | --- | --- |
|  | 10 minutes | 6 days | 14 days |
| Solution with "Aliso B" | 143.1 | 61.4 | 50.1 |
| Solution with no "Aliso B" | 145.9 | 72.9 | 65.3 |

EXAMPLE 4

A solution of 0.3082 parts trans.bis(diethylsulphide) platinum dichloride, 36.12 parts divinyltetramethyldisiloxane, 204.35 parts toluene, is refluxed for 2 hours. A portion of this solution (66.1 parts) is transferred to a bottle and labelled Sample A. A second portion (63.5 parts) is transferred to a bottle and 2.86 parts of a 10% wt:wt solution of "Aliso B" in toluene added and labelled Sample B. Gelation times are determined as described in Example 1 on samples drawn from A and B immediately after preparation and after 1 week. The values found are:

|  | Gelation time, minutes | |
| --- | --- | --- |
|  | Immediately | 1 week |
| Sample A | 45.1 | 56.3 |
| Sample B | 46.1 | 51.4 |

EXAMPLE 5

A cross linkable composition is prepared from 92 parts of a silanol ended polydimethylsiloxane fluid, viscosity 90 cP at 25° C. and 8 parts of a trimethylsilyl ended polymethylhydrogensiloxane fluid of viscosity 20 cP at 25° C. 75 Part portions of this mixture are stirred with 0.5 parts of the catalyst solutions A or B of Example 2. Each of the catalysed mixes contains about 3 p.p.m. platinum. The mixture containing Solution A forms a gel within 20 minutes at 18° C., whilst the mixture containing Solution B had not gelled within 60 minutes at 18° C.

I claim:

1. In an improved platinum catalyst of the type resulting from the admixture of a haloplatinum compound and an aliphatically unsaturated organosiloxane compound, the improvement which comprises the inclusion of an aluminium alkoxide.

2. An improved platinum catalyst as claimed in claim 1 in which the aluminium alkoxide is aluminum triisopropoxide alone or in admixture with aluminium tri-sec. butoxide or is the multicomponent mixture of aluminium alkoxides resulting from forming alkoxides of aluminium with a mixture of isopropanol and secondary butanol.

3. A platinum catalyst comprising the admixture of (a) a haloplatinum compound selected from chloroplatinic acid or alkali metal salt thereof; $PtCl_4$, $PtCl_2$, $H_2PtCl_4$ and its salts; complexes of platinous chloride and olefins or dialkyl sulphides or the analogous bromo compounds of any of the aforementioned chloro compounds; (b) an organopolysiloxane containing one or more vinyl or allyl groups; and (c) an aluminum alkoxide.

4. A platinum catalyst as claimed in claim 3 wherein the organopolysiloxane (b) is divinyltetramethyl disiloxane or 1:3:5:7-tetramethyl-1:3:5:7-tetravinyl-cyclotetrasiloxane.

5. A platinum catalyst as claimed in claim 3 wherein the aluminium alkoxide (c) is aluminium triisopropoxide alone or in admixture with aluminium tri-sec. butoxide or is the multicomponent mixture of aluminium alkoxides resulting from forming alkoxides of aluminium with a mixture of isopropanol and secondary butanol.

6. A platinum catalyst as claimed in claim 3 wherein there is 1 part of component (a) with 30 to 300 parts of component (b) and 1 to 10 parts of component (c), the parts being by weight.

* * * * *